United States Patent [19]

Ito et al.

[11] 4,379,150
[45] Apr. 5, 1983

[54] DIBENZ[B,F][1,4]OXAZEPINE DERIVATIVES, PROCESS FOR PREPARING THE SAME, AND PHARMACEUTICAL COMPOSITIONS COMPRISING THE SAME

[75] Inventors: Kiyohiko Ito, Tama; Masuo Koizumi; Yasushi Murakami, both of Tokyo; Michitaka Akima, Sakado; Jinichiro Aono; Yasuhiro Ohba, both of Kawasaki; Tamotsu Yamazaki, Tokorozawa; Kazushige Sakai, Tokyo; Shun-ichi Hata, Yokohama; Shigeru Takanashi, Asaka, all of Japan

[73] Assignee: Chugai Seiyaku Kabushiki Kaisha, Tokyo, Japan

[21] Appl. No.: 331,897

[22] Filed: Dec. 17, 1981

[30] Foreign Application Priority Data

Dec. 24, 1980 [JP] Japan .................... 55-181831

[51] Int. Cl.³ .................... A61K 31/55; C07D 413/06
[52] U.S. Cl. .................... 424/244; 424/248.54; 424/250; 424/267; 424/274; 260/239.3 T
[58] Field of Search ............ 260/238.3 T; 424/244, 424/274, 267, 248.54, 250

[56] References Cited

U.S. PATENT DOCUMENTS 3,423,402  1/1969  Nagarajan et al. .......... 260/239.3 T

FOREIGN PATENT DOCUMENTS 1670414  10/1970  Fed. Rep. of Germany ... 260/239.3 T
4500M    10/1966  France ................ 260/239.3 T
1042296   9/1966  United Kingdom ........ 260/239.3 T Primary Examiner—Robert T. Bond
Attorney, Agent, or Firm—Browdy and Neimark

[57] ABSTRACT

Dibenz[b,f][1,4]oxazepine derivatives of the formula

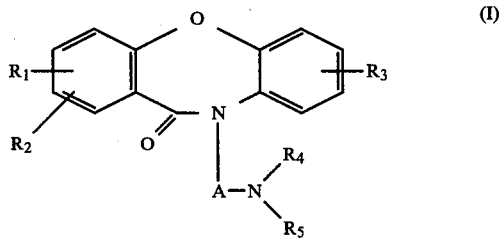

(I)

(wherein $R_1$ is a hydrogen atom or a lower alkyl group; $R_2$ is a branched lower alkyl group; $R_3$ is a hydrogen atom, a carboxyl group, a carbamoyl group, a lower alkoxycarbonyl group, or a lower alkoxy group; $R_4$ and $R_5$ are each a lower alkyl group or may, when taken together with a nitrogen atom, form a heterocyclic ring; and A is a lower alkylene group) or salts thereof, a process for preparing the same and pharmaceutical compositions comprising the same are disclosed. The derivatives of the formula above are effective to prevent and treat circulatory diseases, especially angina pectoris, and therefore, useful as medicines.

10 Claims, No Drawings

DIBENZ[B,F][1,4]OXAZEPINE DERIVATIVES, PROCESS FOR PREPARING THE SAME, AND PHARMACEUTICAL COMPOSITIONS COMPRISING THE SAME

The present invention relates to compounds of the formula:

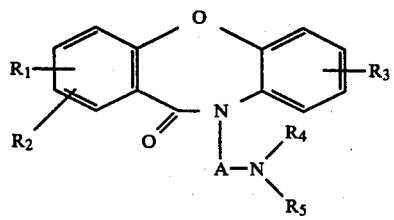
(I)

(wherein $R_1$ is a hydrogen atom or a lower alkyl group; $R_2$ is a branched lower alkyl group; $R_3$ is a hydrogen atom, a carboxyl group, a carbamoyl group, a lower alkoxycarbonyl group, or a lower alkoxy group; $R_4$ and $R_5$ are each a lower alkyl group or may, when taken together with a nitrogen atom, form a heterocyclic ring; and A is a lower alkylene group) or salts thereof.

In the formula (I), the lower alkyl group represented by $R_1$ is a straight or branched alkyl group having 1 to 6 carbon atoms, such as methyl, ethyl, n-propyl, isopropyl, n-butyl, sec-butyl, tert-butyl, isobutyl, n-pentyl, isopentyl, neopentyl and n-hexyl. The branched lower alkyl group represented by $R_2$ is a branched alkyl group having 3 to 6 carbon atoms, such as isopropyl, sec-butyl, tert-butyl, isobutyl, isopentyl, neopentyl, tert-pentyl and sec-pentyl. The lower alkoxycarbonyl group represented by $R_3$ is an alkoxycarbonyl group having 2 to 7 carbon atoms, such as methoxycarbonyl, ethoxycarbonyl, n-propoxycarbonyl, n-butoxycarbonyl, n-pentylcarbonyl, and n-hexylcarbonyl. The lower alkoxy group represented by $R_3$ is a straight or branched alkoxy group having 1 to 6 carbon atoms, such as methoxy, ethoxy, n-propoxy, isopropoxy, n-butoxy, sec-butoxy, tert-butoxy, isobutoxy, n-pentyloxy, sec-pentyloxy, tert-pentyloxy, isopentyloxy, neopentyloxy, and n-hexyloxy. The lower alkyl group represented by $R_4$ and $R_5$ is a straight or branched alkyl having 1 to 4 carbon atoms, such as methyl, ethyl, n-propyl, isopropyl, n-butyl, sec-butyl, tert-butyl, and isobutyl. Examples of the heterocyclic ring formed by $R_4$ and $R_5$ when they are taken together with a nitrogen atom are piperidino, piperazino, pyrrolidino and morpholino. The lower alkylene group represented by A is a straight or branched alkylene group having 2 to 6 carbon atoms, such as ethylene, trimethylene, tetramethylene, pentamethylene and hexamethylene.

The compounds of the present invention that are represented by the formula (I) are novel compounds effective to prevent and treat circulatory diseases, especially angina pectoris.

Conventionally known dibenz[b,f][1,4]oxazepine-11(10H)-one derivatives, particularly those having an alkylaminoalkyl group bonded to 10-position, are 10-[2-(dimethylamino)ethyl or 3-(dimethylamino)propyl]-2-methyl-dibenz[b,f][1,4]-oxazepine-11(10H)-one [$R_1$=H, $R_2$=CH$_3$, $R_3$=H, $R_4$=$R_5$=CH$_3$, A=(CH$_2$)$_2$ or (CH$_2$)$_3$ in the formula (I)]; see Swiss Pat. No. 421,109. These compounds are said to have emotion control and antidepression activities, but no data has been presented to support these activites. The present inventors have made experiments to prepare a series of dibenz[b,f][1,4]-oxazepine derivatives and test their pharmacological efficacies to review the correlation of their structure-activity. As a result, they have found that compounds having a branched lower alkyl group introduced in the benzene nucleus have desired effects on circulatory organs.

The compounds of the present invention having the formula (I) are prepared by reacting, for example, a compound of the formula (II):

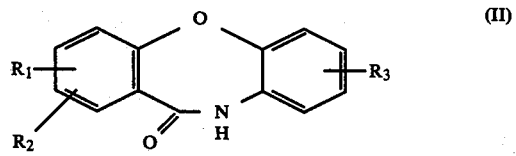
(II)

(wherein $R_1$, $R_2$ and $R_3$ have the same meanings as defined above) with a compound of the formula (III):

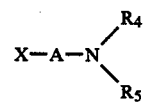

(wherein A, $R_4$ and $R_5$ have the same meanings as defined above; X is a halogen atom). The reaction is usually performed in the presence of a solvent such as dimethylformamide, dimethyl sulfoxide or dioxane at a temperature between room temperature and 150° C., preferably between 50° and 100° C. Preferably, the compound (II) is preliminarily reacted with an alkali metal into an alkali derivatives. Suitable alkali metal sources include sodium amide, sodium hydride, metallic sodium, sodium alcoholate, sodium carbonate, potassium carbonate, sodium hydrogencarbonate, potassium hydrogencarbonate, sodium hydroxide, potassium hydroxide, sodium acetate and potassium acetate.

Many of the compounds (II) are also novel compounds which are prepared by taking the following reaction scheme (wherein the same symbols as used in formula (I) have the same meanings; and M is an alkali metal):

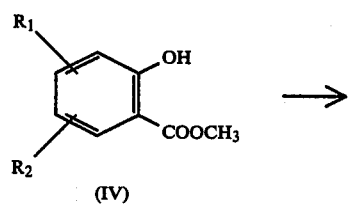
(IV)

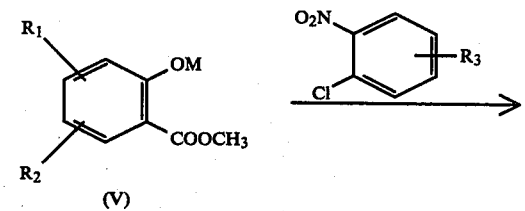
(V)

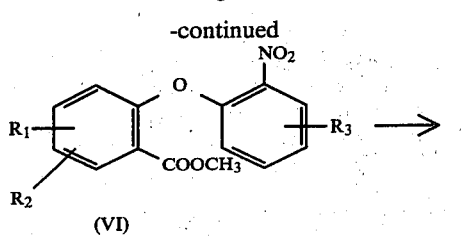

(VI)

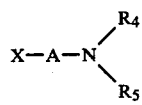

(VII)

To be more specific, a compound of the formula (IV) is converted to an alkali metal salt of the formula (V) which is reacted with an equimolar amount of substituted nitrochlorobenzene in the absence of a solvent or in the presence of a solvent such as benzene xylene dimethylformamide or dioxane at a temperature between 80° and 180° C., to thereby obtain a compound of the formula (VI). A good result is obtained if a copper compound is used as a catalyst for the conversion of the compound (V) to the compound (VI). Then, the compound (VI) is catalytically reduced to a compound (VII) in a hydrogen stream at atmospheric or higher pressure in the presence of a catalyst such as palladium-carbon or Raney-nickel. The compound (VII) is subjected to ring formation in the absence of a solvent or in the presence of a solvent at a temperature between 100° and 250° C., preferably between 150° and 200° C., to thereby produce a compound of the formula (II).

The compound of the formula (I) can also be prepared by reacting a compound of the formula (VIII):

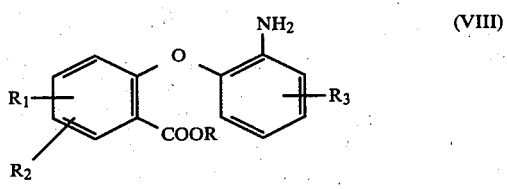

(wherein $R_1$, $R_2$ and $R_3$ have the same meanings as defined above; and R is a lower alkyl group) with a compound of the formula (III):

$$X-A-N\begin{matrix}R_4\\R_5\end{matrix}$$

(wherein $R_4$, $R_5$, A and X have the same meanings as defined above). The reaction is usually performed in a solvent such as dimethylformamide, dimethyl sulfoxide or dioxane in the presence of an alkali metal at a temperature between room temperature and 150° C., preferably between 50° and 100° C. Suitable alkali metal sources include sodium amide, sodium hydride, metallic sodium, sodium alcoholate, sodium carbonate, potassium carbonate, sodium hydrogencarbonate, potassium hydrogencarbonate, sodium hydroxide, potassium hydroxide, sodium acetate, and potassium acetate.

The so prepared compounds of the present invention are useful as a medicine to prevent and treat circulatory diseases, especially angina pectoris. The compounds can be used as a medicine in the form of tablet, granule, powder, capsule or injection that is made by a known method after they are blended with a pharmaceutically acceptable carrier and an optional adjuvant. Preferred pharmaceutical carriers for making tablet, granule, powder and capsule are lactose, starch, dextrin, mannitol, sucrose, crystalline cellulose, kaolin, calcium carbonate, talc, and magnesium stearate. For making an injection, the compounds are preferably dissolved in distilled water or an aqueous solution of salts such as sodium chloride and potassium chloride. The compounds are contained in these formulations in a convenient unit dose that varies with the age of the patient and the severity of his diseases. The daily dose of the compounds is preferably between 100 and 1000 mg for oral administration, and between 10 and 200 mg for intravenous injection.

The present invention is now described in greater detail by reference to the following experiment and examples to which the present invention is by no means limited.

Experiment

The effect of the compounds of the present invention to inhibit coronary vasoconstriction was studied. That vasoconstriction was induced by acetylcholine 0.3 μg in isolated, donor-perfused rat hearts (K. Sakai, Brit. J. Pharmacol., 68, 625–638, 1980), and determined by measuring the arterial perfusion pressure with a pressure transducer (Nihon Kohden MPU—0.5). The compounds of the present invention were administered in the artery in an amount between 30 and 60 μg. The results are shown in Table 1.

TABLE 1

| Sample | Dose (μg) | Inhibition* |
|---|---|---|
| Comp. of Ex. 1 | 30 | ++++ |
| Comp. of Ex. 2 | 30 | +++ |
| Comp. of Ex. 3 | 30 | ++++ |
| Comp. of Ex. 4 | 60 | ++ |
| Comp. of Ex. 5 | 30 | ++ |
| Comp. of Ex. 8 | 30 | +++ |
| Comp. of Ex. 9 | 30 | ++++ |
| Comp. of Ex. 10 | 30 | ++ |
| Comp. of Ex. 14 | 30 | +++ |
| Comp. of Ex. 15 | 30 | ++ |
| Comp. of Ex. 17 | 30 | ++ |
| dipyridamole | 60 | ± |

*++: 20–30% inhibited
+++: 31–40% inhibited
++++: 41% or more inhibited

Thirty micrograms of an intraarterial injection of the compounds of the present invention proved very effective in suppressing coronary vasoconstriction without presenting an undesired effect similar to that of atropine. Thus, the compounds can be used as a medicine to prevent and treat variant antina pectoris by virtue of a new mechanism. The toxicity of the compounds was found to be very low since the $LD_{50}$ for oral administration to rats was 1 g/kg or more.

EXAMPLE 1

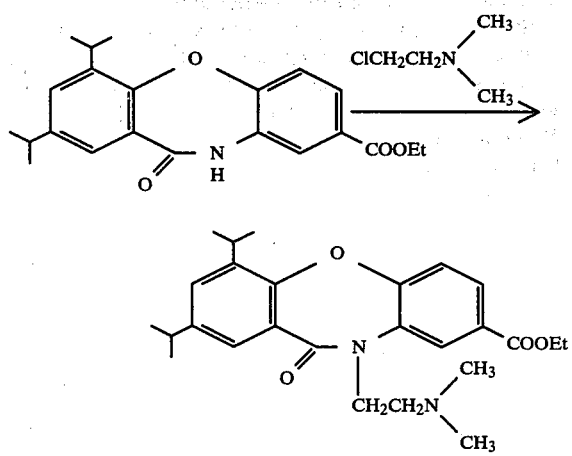

Two grams of 60% sodium hydride/mineral oil that was washed once with dry n-hexane was suspended in 100 ml of dry dimethylformamide. To the suspension, 18.4 g of 2,4-diisopropyl-8-ethoxycarbonyl-dibenz[b,f][1,4]oxazepine-11(10H)-one was added gradually under a nitrogen stream with stirring, and the mixture was heated at 60° C. for 30 minutes. Then, 21.6 g of dimethylaminoethyl chloride hydrochloride that was treated with 50% potassium hydroxide into a free base was extracted with 50 ml of toluene, and the extract was added to the previously prepared mixture, and the resulting reaction mixture was heated at 80° C. for 7 hours with stirring. The reaction mixture was concentrated under reduced pressure to give a oily residue, which was extracted with 500 ml of benzene. The extract was washed with 200 ml of water three times, and dried over anhydrous Glauber's salt. Then, benzene was distilled off to give 2,4-diisopropyl-10[2-(dimethylamino)ethyl]-8-ethoxycarbonyl-dibenz[b,f][1,4]oxazepine-11(10H)-one as an oil. The product was dissolved in 30 ml of 10% hydrochloric acid-ethanol, and then was added 100 ml of ethyl ether. The resulting crystal was filtered off, and dried to obtain 16 g of a hydrochloride of the product in a yield of 67.2%. Recrystallization from isopropyl alcohol gave a substance having m.p. 233°–234° C. (with decomposition).

Elemental analysis:
Calculated for $C_{26}H_{34}N_2O_4 \cdot HCl$: C 65.74, H 7.43, N 5.90(%); Found: C 65.61, H 7.49, N 5.90(%).

EXAMPLES 2 TO 14

The compounds indicated below were prepared as in Example 1.

TABLE

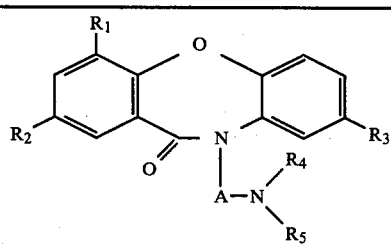

| Ex. No. | $R_1$ | $R_2$ | $R_3$ | $R_4$ | $R_5$ | A | m.p. (°C.) | yield (%) | molecular formula | elemental analysis (%) | C | H | N |
|---|---|---|---|---|---|---|---|---|---|---|---|---|---|
| 2 | i-$C_3H_7$ | i-$C_3H_7$ | H | $CH_3$ | $CH_3$ | $C_2H_4$ | 204 | 72.2 | $C_{23}H_{30}O_2N_2 \cdot HCl \cdot \frac{1}{2}H_2O$ | calculated | 67.72 | 7.91 | 6.87 |
|  |  |  |  |  |  |  |  |  |  | found | 68.01 | 7.61 | 6.81 |
| 3 | i-$C_3H_7$ | i-$C_3H_7$ | H | $CH_3$ | $CH_3$ | $C_3H_6$ | 183 | 72.0 | $C_{24}H_{32}O_2N_2 \cdot HCl \cdot \frac{1}{2}H_2O$ | calculated | 67.68 | 8.05 | 6.58 |
|  |  |  |  |  |  |  |  |  |  | found | 67.46 | 7.84 | 6.56 |
| 4 | i-$C_3H_7$ | i-$C_3H_7$ | $OCH_3$ | $CH_3$ | $CH_3$ | $C_2H_4$ | 237 | 64.00 | $C_{24}H_{32}O_3N_2 \cdot HCl \cdot \frac{1}{2}H_2O$ | calculated | 65.22 | 7.75 | 6.34 |
|  |  |  |  |  |  |  |  |  |  | found | 65.46 | 7.58 | 6.17 |
| 5 | i-$C_3H_7$ | i-$C_3H_7$ | $OCH_3$ | $CH_3$ | $CH_3$ | $C_3H_6$ | 218 | 44.0 | $C_{25}H_{34}O_3N_2 \cdot HCl \cdot \frac{1}{2}H_2O$ | calculated | 65.85 | 7.96 | 6.14 |
|  |  |  |  |  |  |  |  |  |  | found | 65.62 | 7.81 | 6.07 |
| 6 | i-$C_3H_7$ | i-$C_3H_7$ | $COOC_2H_5$ | ⬡ | | $C_2H_4$ | 216 (with decomposition) | 85.3 | $C_{29}H_{38}O_4N_2 \cdot HCl$ | calculated | 67.63 | 7.63 | 5.44 |
|  |  |  |  |  |  |  |  |  |  | found | 67.43 | 7.69 | 5.48 |
| 7 | i-$C_3H_7$ | i-$C_3H_7$ | $COOC_2H_5$ | ⬠ | | $C_2H_4$ | 222 (with decomposition) | 84.3 | $C_{28}H_{36}O_4N_2 \cdot HCl$ | calculated | 67.12 | 7.44 | 5.59 |
|  |  |  |  |  |  |  |  |  |  | found | 67.08 | 7.46 | 5.56 |
| 8 | H | t-$C_5H_{11}$ | $COOC_2H_5$ | $CH_3$ | $CH_3$ | $C_2H_4$ | 127 | 50.0 | $C_{25}H_{32}O_4N_2 \cdot HCl \cdot 3/2H_2O$ | calculated | 61.53 | 7.44 | 5.74 |
|  |  |  |  |  |  |  |  |  |  | found | 61.25 | 7.18 | 5.83 |
| 9 | H | t-$C_5H_{11}$ | $COOC_2H_5$ | $CH_3$ | $CH_3$ | $C_3H_6$ | amorphous powder | 56.0 | $C_{26}H_{34}O_4N_2 \cdot HCl \cdot 3/2H_2O$ | calculated | 62.22 | 7.63 | 5.58 |
|  |  |  |  |  |  |  |  |  |  | found | 62.51 | 7.56 | 5.84 |
| 10 | H | t-$C_5H_{11}$ | H | $CH_3$ | $CH_3$ | $C_3H_6$ | amorphous powder | 69.8 | $C_{23}H_{30}O_2N_2 \cdot HCl \cdot 3/2H_2O$ | calculated | 64.25 | 7.97 | 6.52 |
|  |  |  |  |  |  |  |  |  |  | found | 64.26 | 7.72 | 6.55 |
| 11 | t-$C_4H_9$ | t-$C_4H_9$ | $COOC_2H_5$ | $CH_3$ | $CH_3$ | $C_2H_4$ | 206 | 55.9 | $C_{28}H_{38}O_4N_2 \cdot HCl$ | calculated | 66.85 | 7.81 | 5.57 |
|  |  |  |  |  |  |  |  |  |  | found | 66.63 | 7.92 | 5.43 |
| 12 | H | t-$C_4H_9$ | $COOC_2H_5$ | $CH_3$ | $CH_3$ | $C_2H_4$ | 127 | 59.6 | $C_{24}H_{30}O_4N_2 \cdot HCl \cdot H_2O$ | calculated | 62.00 | 7.15 | 6.02 |
|  |  |  |  |  |  |  |  |  |  | found | 61.76 | 6.86 | 5.93 |
| 13 | H | t-$C_4H_9$ | $COOC_2H_5$ | $CH_3$ | $CH_3$ | $C_3H_6$ | 179 | 50.6 | $C_{25}H_{32}O_4N_2 \cdot HCl$ | calculated | 65.14 | 7.21 | 6.07 |
|  |  |  |  |  |  |  |  |  |  | found | 64.87 | 7.38 | 5.85 |
| 14 | i-$C_3H_7$ | i-$C_3H_7$ | $COOC_2H_5$ | $CH_3$ | $CH_3$ | $C_3H_6$ | 124 | 55.6 | $C_{27}H_{36}N_2O_4 \cdot HCl$ | calculated | 66.31 | 7.62 | 5.72 |
|  |  |  |  |  |  |  |  |  |  | found | 66.07 | 7.34 | 5.68 |

EXAMPLE 15

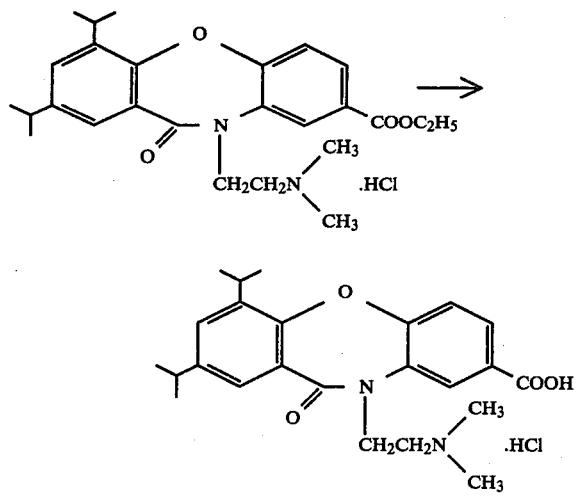

A mixture of 6 g of 2-4-diisopropyl-10-[2-dimethylaminoethyl]-8-ethoxycarbonyl-dibenz[b,f][1,4]oxazepine-11(10H)-one hydrochloride obtained in Example 1, 60 ml of ethanol, and 60 ml of 10% aqueous sodium hydroxide was refluxed for one hour. The mixture was made acidic with diluted hydrochloric acid, and after distilling ethanol off, the mixture was extracted with chloroform containing 5% ethanol. The extract washed with saturated brine and dried over anhydrous Glauber's salt evaporated off to give 5 g of 2,4-diisopropyl-10-[2-(dimethylamino)ethyl]-8-carboxy-dibenz[b,f][1,4]-oxazepine-11(10H)-one hydrochloride in a yield of 88.8% m.p. 245° C. (with decomposition) after recrystallization from acetone.

Elemental analysis:
Calculated for $C_{24}H_{30}O_4N_2 \cdot HCl$: C 64.49, H 6.99, N 6.27(%); Found: C 64.48, H 6.97, N 6.23(%).

EXAMPLE 16

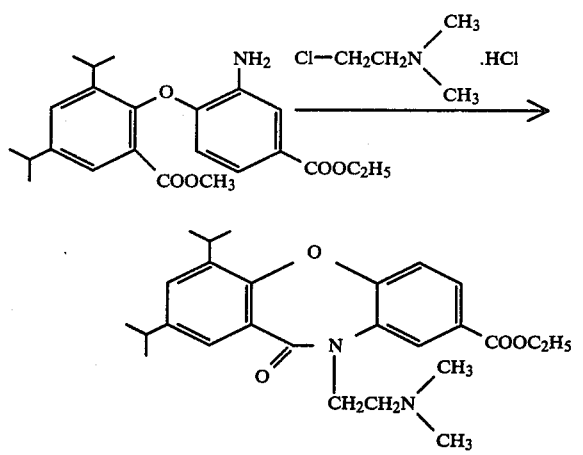

Two hundred milligrams of 60% sodium hydride/mineral oil was washed with dry n-hexane once and suspended in 10 ml of dry dimethylformamide. To the suspension, 2 g of methyl 3,5-diisopropyl-2-(4'-ethoxycarbonyl-2'-aminophenoxy)benzoate was added under a nitrogen stream with stirring, and the mixture was heated at 60° C. for one hour. Then, 720 mg of dimethylaminoethyl chloride hydrochloride that was treated with 50% potassium hydroxide into a free base was extracted with 10 ml of toluene, and the extract was added to the previously prepared mixture, and the resulting reaction mixture was heated at 70° C. for 7 hours with stirring. The reaction mixture was cooled, mixed with 50 ml of toluene. Toluene layer was washed with 50 ml of water three times, dried over anhydrous Glauber's salt, and then distilled off under vacuum to produce an oily product. The product was purified by column chromatography on silica gel using chloroform-methanol as eluent to give 1.5 g of 2,4-diisopropyl-10-[2-(dimethylamino)ethyl]-8-ethoxycarbonyl-dibenz[b,f][1,4]-oxazepine-11(10H)-one in a yield of 68.2%. Recrystallization from ethanol-water produced a substrate having m.p. 97°-98° C. The substance was dissolved in 5 ml of 10% hydrochloric acid-ethanol, and the solution was mixed with ethyl ether to produce a hydrochloride of the substance having m.p. 233°-234° C. (with decomposition). IR analysis of the hydrochloride showed that it was identical with the product of Example 1.

EXAMPLE 17

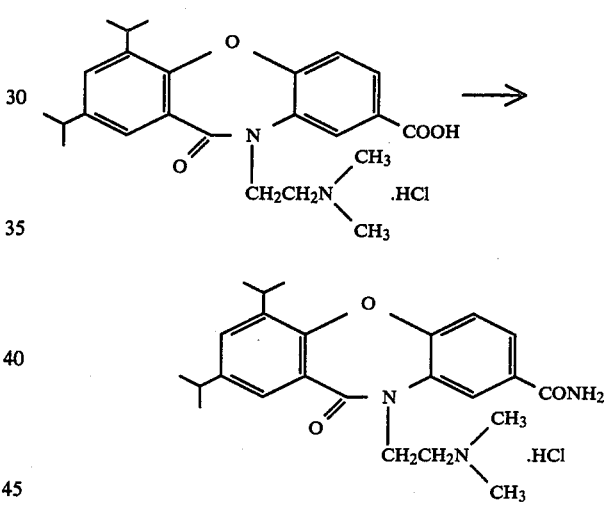

A mixture of 2 g of the 2,4-diisopropyl-10-[2-(dimethylamino)ethyl]-8-carboxy-dibenz[b,f][1,4]oxazepine-11(10H)-one hydrochloride obtained in Example 14, 30 ml of chloroform and 10 ml of thionyl chloride was refluxed for 3 hours. The reaction mixture was concentrated to dryness under vacuum, and the residue was mixed with 6 g of ammonium carbonate and 20 ml of chloroform, and the mixture was stirred overnight at room temperature. Then, the reaction mixture was washed with water, dried over anhydrous Glauber's salt, and distilled off to obtain the residue as an oil. The oil was purified by column chromatography on silica gel using chloroform-methanol as an eluent to obtain 1 g of 2,4-diisopropyl-10-[2-(dimethylamino)ethyl]-8-carbamoyl-dibenz[b,f][1,4]oxazepine-11(10H)-one as an oil in a yield of 54.6%. The oil was dissolved in 4 ml of 10% hydrochloric acid-ethanol and left to stand until a hydrochloride of the oxazepine was produced in a crystalline form. m.p. 223°-225° C.

What is claimed is:
1. A compound of the formula:

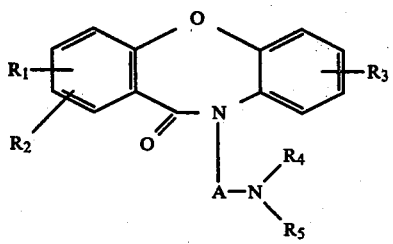

(wherein $R_1$ is a hydrogen atom or a lower alkyl group; $R_2$ is a branched lower alkyl group; $R_3$ is a hydrogen atom, a carboxyl group, a carbamoyl group, a lower alkoxycarbonyl group or a lower alkoxy group with the proviso that both $R_1$ and $R_3$ are not hydrogen; $R_4$ and $R_5$ are each a lower alkyl group or may, when taken together with a nitrogen atom, form a heterocyclic ring selected from the group consisting of piperidino, piperazino, pyrrolidino or morpholino; A is a lower alkylene group) or a pharmaceutically acceptable salt thereof.

2. A compound according to claim 1 which is represented by the formula:

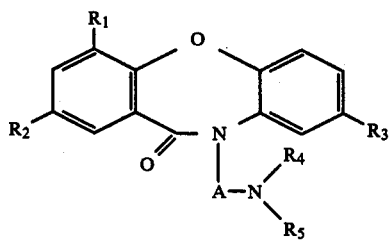

or a pharmaceutically acceptable salt thereof.

3. A compound according to claim 1 which is represented by the formula:

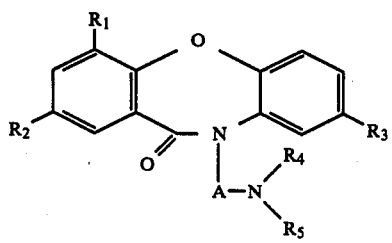

(wherein $R_1$ is a hydrogen or an alkyl group having 1 to 6 carbon atoms; $R_2$ is a branched alkyl group having 3 to 6 carbon atoms; $R_3$ is a hydrogen atom, a carboxyl group, a carbamoyl group, an alkoxycarbonyl group having 2 to 7 carbon atoms or an alkoxy group having 1 to 6 carbon atoms; $R_4$ and $R_5$ are each an alkyl group having 1 to 4 carbon atoms, or may, when taken together with a nitrogen atom, form a said heterocyclic ring; A is an alkylene group having 2 to 6 carbon atoms) or a pharmaceutically acceptable salt thereof.

4. A compound according to claim 1 which is represented by the formula:

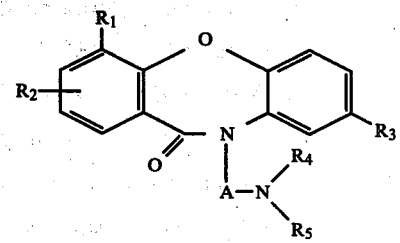

(wherein $R_1$ is a hydrogen atom, isopropyl or tert-butyl; $R_2$ is isopropyl, tert-butyl or tert-pentyl; $R_3$ is a hydrogen atom, methoxy, ethoxycarbonyl, carboxyl or carbamoyl; $R_4$ and $R_5$ are methyl or, when taken together with a nitrogen atom, form piperidyl or pyrrolidinyl; A is ethylene or propylene) or a pharmaceutically acceptable salt thereof.

5. A process for preparing a compound of the formula:

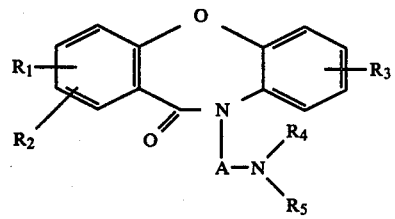

(wherein $R_1$ is a hydrogen atom or a lower alkyl group; $R_2$ is a branched lower alkyl group; $R_3$ is a hydrogen atom, a carboxyl group, a carbamoyl group, a lower alkoxycarbonyl group or a lower alkoxy group; $R_4$ and $R_5$ are each a lower alkyl group or may, when taken together with a nitrogen atom, form a heterocyclic ring selected from the group consisting of piperidino, piperazino, pyrrolidino or morpholino; A is a lower alkylene group) or a salt thereof by reacting a compound of the formula:

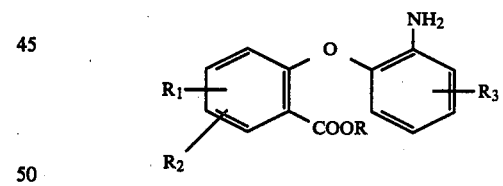

(wherein $R_1$, $R_2$ and $R_3$ have the same meanings as defined above; R is a lower alkyl group) with a compound of the formula:

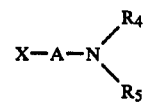

(wherein A, $R_4$, $R_5$ and X have the same meanings as defined above).

6. A process according to claim 5 wherein the reaction is performed in a solvent such as dimethylformamide, dimethyl sulfoxide and dioxane.

7. A process according to claim 5 wherein the reaction is performed at a temperature between room temperature and 150° C.

8. A process according to claim 7 wherein the reaction temperature is between 50° and 100° C.

9. A process according to claim 5 wherein the reaction is performed in the presence of an alkali metal source such as sodium amide, sodium hydride, metallic sodium, sodium alcoholate, sodium carbonate, potassium carbonate, sodium hydrogencarbonate, potassium hydrogencarbonate, sodium hydroxide, potassium hydroxide, sodium acetate and potassium acetate.

10. A pharmaceutical composition for preventing and treating circulatory diseases which comprises an amount effective for preventing or treating a circulatory disease of a compound of the formula:

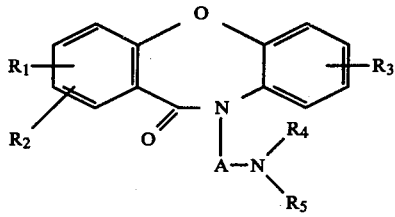

(wherein $R_1$ is a hydrogen atom or a lower alkyl group; $R_2$ is a branched lower alkyl group; $R_3$ is a hydrogen atom, a carboxyl group, a carbamoyl group, a lower alkoxycarbonyl group or a lower alkoxy group with the proviso that both $R_1$ and $R_3$ are not hydrogen; $R_4$ and $R_5$ are each a lower alkyl group or may, when taken together with a nitrogen atom, form a piperidino, piperazino, pyrrolidino or morpholino ring; A is a lower alkylene group) or a pharmaceutically acceptable salt thereof, and a pharmaceutically acceptable carrier.

* * * * *